United States Patent [19]

Grayhack et al.

[11] Patent Number: 4,611,594
[45] Date of Patent: Sep. 16, 1986

[54] MEDICAL INSTRUMENT FOR CONTAINMENT AND REMOVAL OF CALCULI

[75] Inventors: John T. Grayhack, La Grange; Theodore V. Benderev, Chicago, both of Ill.

[73] Assignee: Northwestern University, Evanston, Ill.

[21] Appl. No.: 599,020

[22] Filed: Apr. 11, 1984

[51] Int. Cl.⁴ ............................................. A61B 17/00
[52] U.S. Cl. .................................... 128/328; 128/345
[58] Field of Search ............... 128/328, 320, 356, 345; 604/107

[56] References Cited

U.S. PATENT DOCUMENTS

| | | | |
|---|---|---|---|
| 2,918,919 | 12/1959 | Wallace | 128/328 |
| 2,943,626 | 7/1960 | Dormia | 128/328 |
| 3,074,408 | 1/1963 | Chester | 128/328 |
| 3,334,630 | 8/1967 | Kramer | 128/328 |
| 3,827,437 | 8/1974 | Inaba | 128/328 |
| 4,046,150 | 9/1977 | Schwartz | 128/328 |
| 4,243,040 | 1/1981 | Beecher | 128/328 |
| 4,469,100 | 9/1984 | Hardwick | 128/328 |

FOREIGN PATENT DOCUMENTS

| | | | |
|---|---|---|---|
| 1566147 | 7/1970 | Fed. Rep. of Germany | 128/328 |
| 2057636 | 3/1972 | Fed. Rep. of Germany | 128/328 |
| 2127125 | 5/1973 | Fed. Rep. of Germany | 128/328 |
| 1272412 | 8/1961 | France | 128/328 |

Primary Examiner—Michael H. Thaler
Attorney, Agent, or Firm—Tilton, Fallon, Lungmus

[57] ABSTRACT

Several versions of instruments are disclosed which are useful for the containment of calculi to minimize injury to surrounding tissue during removal and/or destruction of such calculi. In each embodiment a suitable grasping device is utilized to locate and grasp a stone (calculus) in a body passage or organ, such grasping device being used in combination with a catheter having an expandable and contractable distal end portion capable of receiving and substantially enclosing the stone to protect the surrounding tissue from injury that might otherwise be produced by the rough edges of the stone as it is extracted, or to shield such tissue as the stone is fragmented in situ and then contain the fragments as they are removed.

8 Claims, 21 Drawing Figures

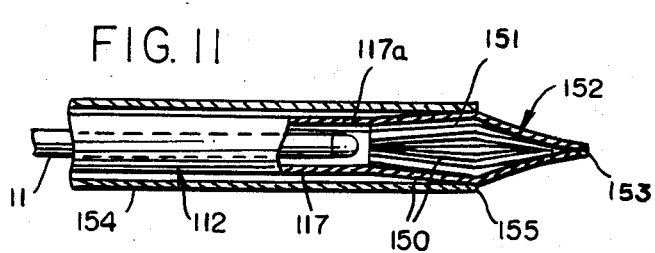
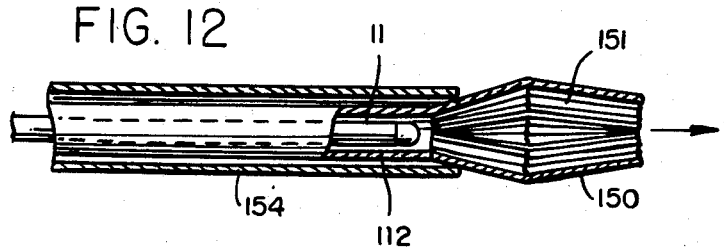
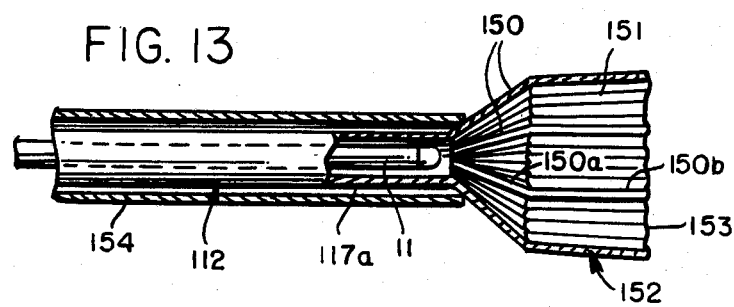
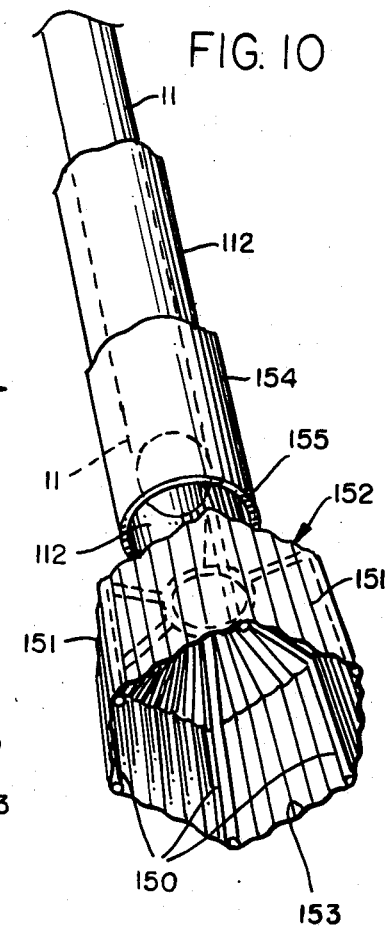
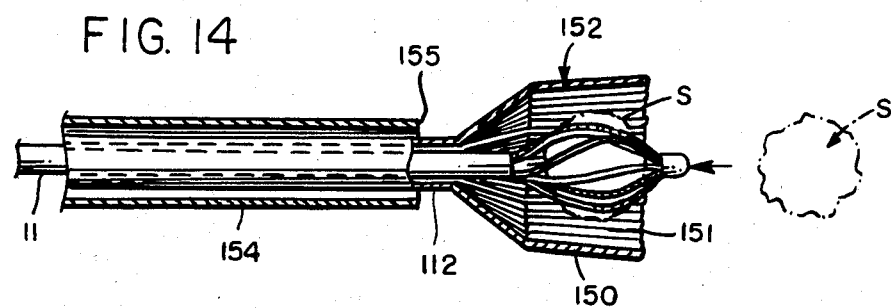
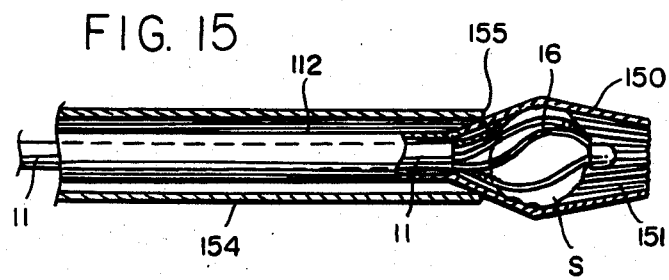

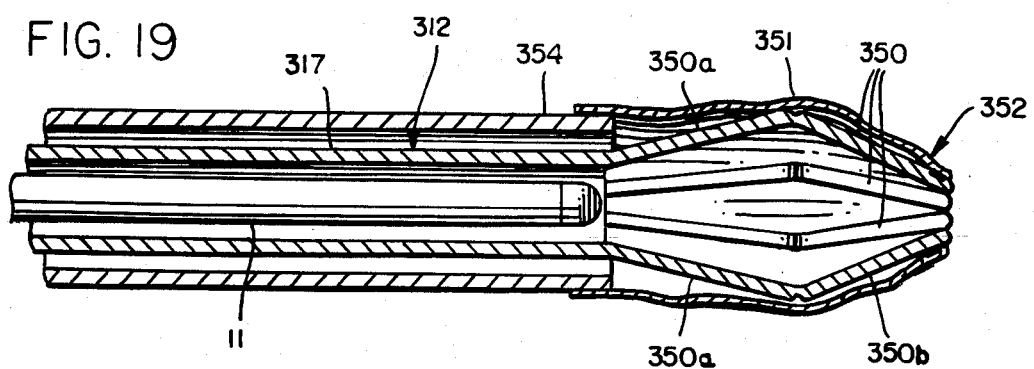
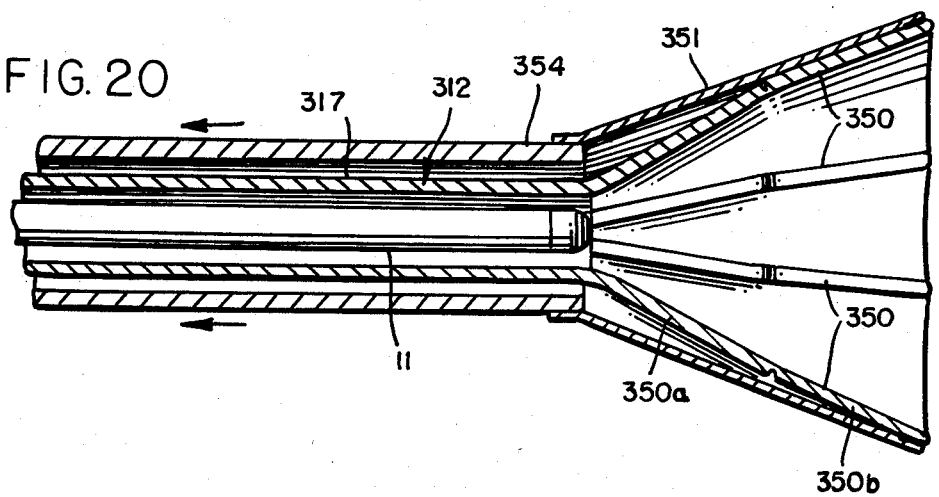
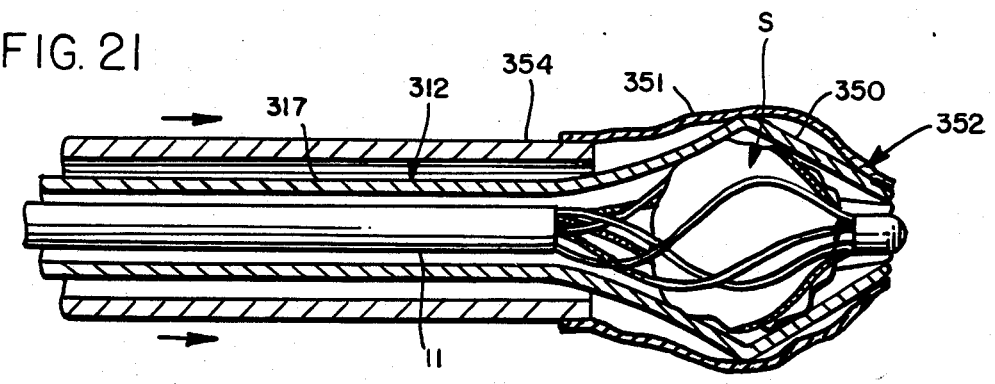

MEDICAL INSTRUMENT FOR CONTAINMENT AND REMOVAL OF CALCULI

BACKGROUND AND SUMMARY

Instruments for removing calculi (e.g., kidney and gallstones) without major surgery are commonly of two general types. One takes the form of an expandable basket as shown and described in patents to Dormia No. 2,943,626, Wallace No. 2,918,919, and Schwartz et al No. 4,046,150. The other form consists of miniaturized grasping forceps having an elongated flexible stem which allow the forceps to be inserted through endoscope passages and through natural or artificially-formed body passages, as disclosed in patents such as Kramer No. 3,334,630, and Chester No. 3,074,408. One problem associated with both types of instruments lies in the possible injury to surrounding tissue as a grasped stone is extracted through the body passage or organ. Such dangers may be reduced by fragmenting the stone in situ with a lithotriptor, but such fragmentation may create additional problems if any of the fragments should remain, provide the nuclei for further stone development, and ultimately occlude the body passages.

Accordingly, it is an object of this invention to provide an instrument that may be used to contain a stone while it remains within the organ or body passage, thereby protecting the surrounding tissues against direct contact with the edges and surfaces of that stone. The instrument may then be used to remove the grasped and contained stone in an unfragmented condition or, alternatively, to fragment the stone in situ with a suitable lithotriptor. If the stone is removed intact, the instrument shields the surrounding tissues against contact that might result in cutting or tearing of such tissues, whereas if the stone is first fragmented, the instrument may be used to contain and extract such fragments.

In brief, one component of the instrument takes the form of an elongated stone-grasping device having a distal working end for grasping calculi. Such a device may be any of a variety of conventional stone baskets or grasping forceps of the types mentioned above. A second component takes the form of a catheter having a lumen which slidably receives the grasping device. The distal end of the catheter terminates in an opening through which the working end of the grasping device may be extended and retracted for the purpose of grasping a stone and drawing it into the end portion of the catheter. The catheter's distal end portion is expandable to receive a stone retained by the working end of the grasping device and contractable to retain the stone or its fragments during an extraction procedure. In the case of fragmentation of the stone prior to extraction, the distal end of the catheter may also serve to protect surrounding tissue from injury that might otherwise be caused by the fragmenting element or the energy release therefrom.

In one embodiment, the distal end portion of the catheter is provided with one or more expandable gussets that permit enlargment of the catheter's distal end as the working end of the grasping device, and the stone grasped thereby, are retracted into the catheter. In another embodiment, the catheter is provided at its distal end with a plurality of circumferentially-spaced flexible struts that, in an untensioned state, spread apart to define an open-ended basket. Adjacent struts of the basket are bridged by a flexible membrane or web. A flexible actuating tube is slidably mounted upon the catheter and engages the struts to close or contract the basket when the tube is shifted distally along the catheter. In a third embodiment, the catheter again has a plurality of flexible struts at its distal end but, unlike the second version, such struts in an untensioned condition have their ends in mutual engagement so that the basket is normally closed. Actuating means in the form of control lines extend longitudinally along the catheter from the struts to the catheter's proximal end so that upon manipulation of such lines the basket may be opened to receive and enclose a stone drawn into the basket by the grasping device. A fourth embodiment is similar to the third, with struts that urge the basket into a normally closed condition, but the actuating means includes an outer actuating tube connected to the struts by the protective membrane that extends over the basket. When the actuating tube is retracted, the membrane is tensioned and the struts are flexed outwardly to open the basket so that the basket may receive and enclose a stone drawn into it by the grasping device.

Other features, objects, and advantages of the invention will become apparent from the drawings and specification.

DRAWINGS

FIGS. 3–6 schematically depict successive stages in the operation of the instrument.

Figure 7:
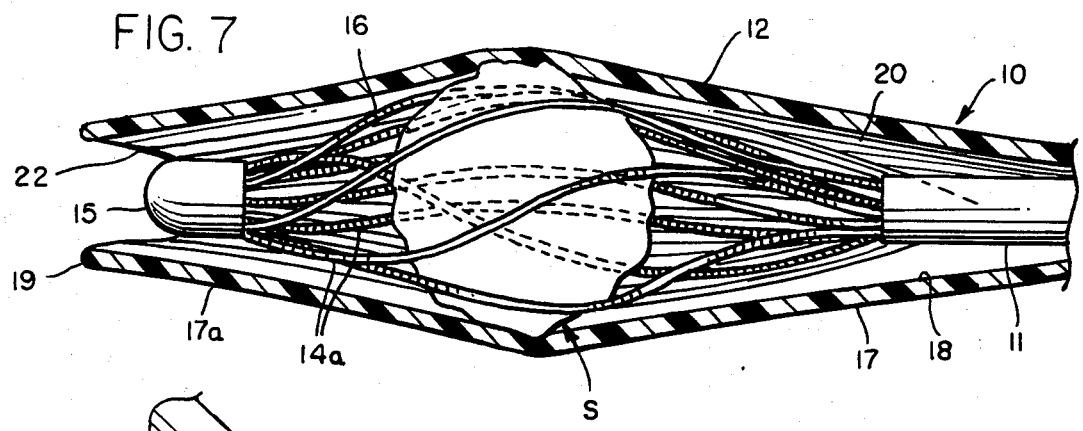

FIG. 7 is an enlarged longitudinal sectional view showing a stone held by a grasping device and contained within the distal end of the catheter.

Figure 8:
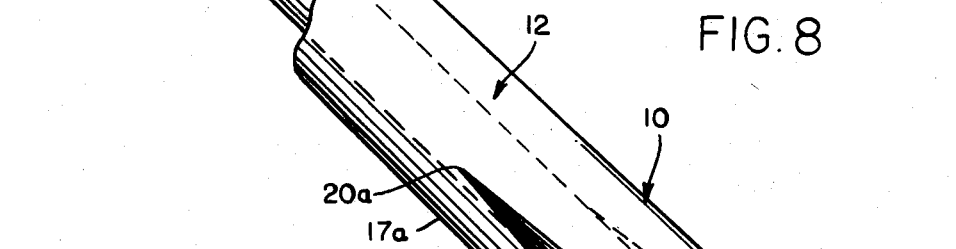

FIG. 8 is a perspective view of the instrument with the catheter in a relaxed or unstretched state.

Figure 9:
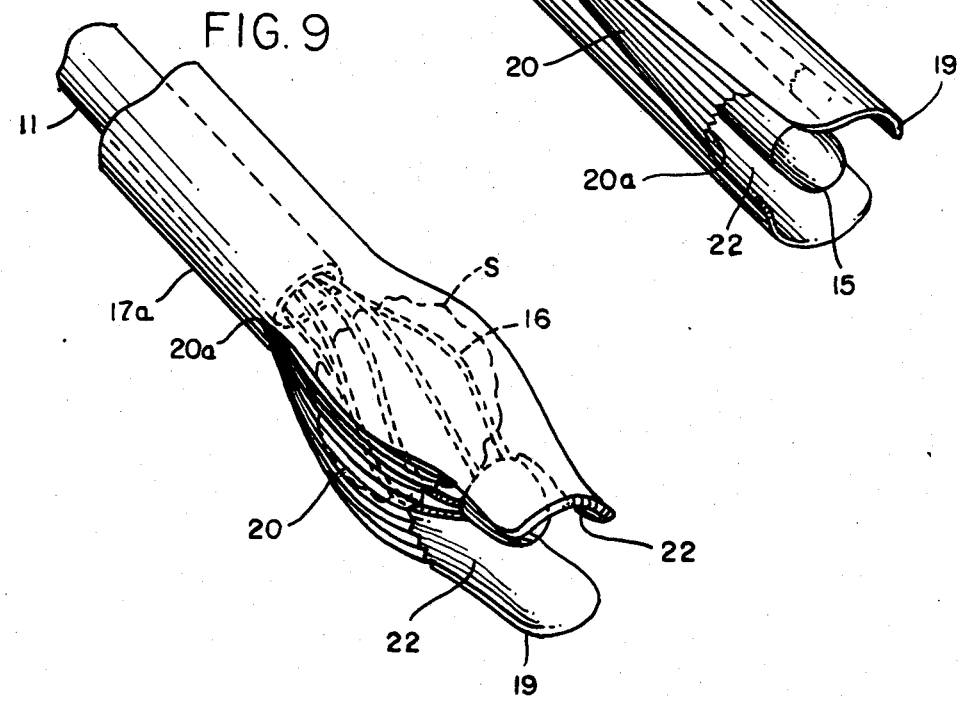

FIG. 9 is a perspective view showing the distal end of the catheter in the same orientation as depicted in FIG. 8 but with the catheter in a stretched or expanded condition.

FIG. 10 is a perspective view showing the distal end of an instrument constituting a second embodiment of the invention, the basket-providing distal end of the catheter being shown in fully open condition.

FIGS. 11–15 are longitudinal sectional views showing a sequence of steps and conditions of the instrument in use, with FIG. 13 being a sectional view of the instrument generally in the condition illustrated in FIG. 10.

Figure 16:
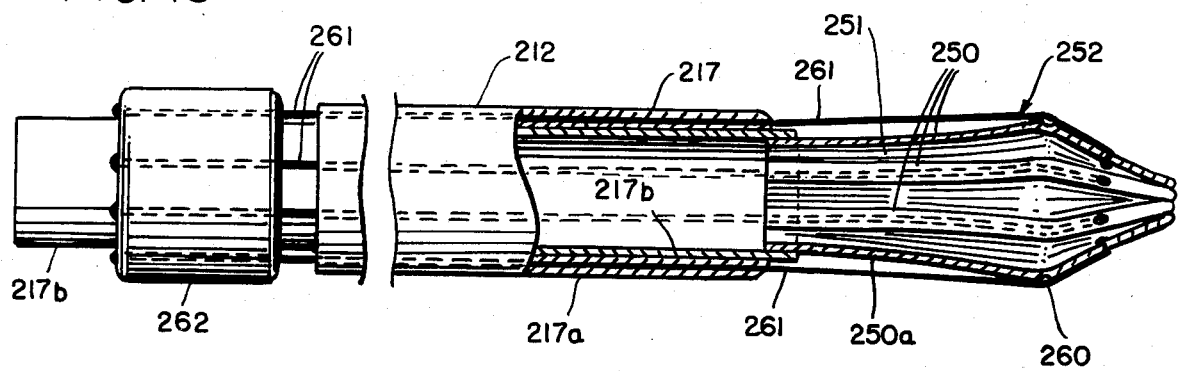

FIG. 16 is a fragmentary longitudinal sectional view of a third embodiment with the basket at the distal end of the catheter being shown in a collapsed or closed condition.

Figure 17:
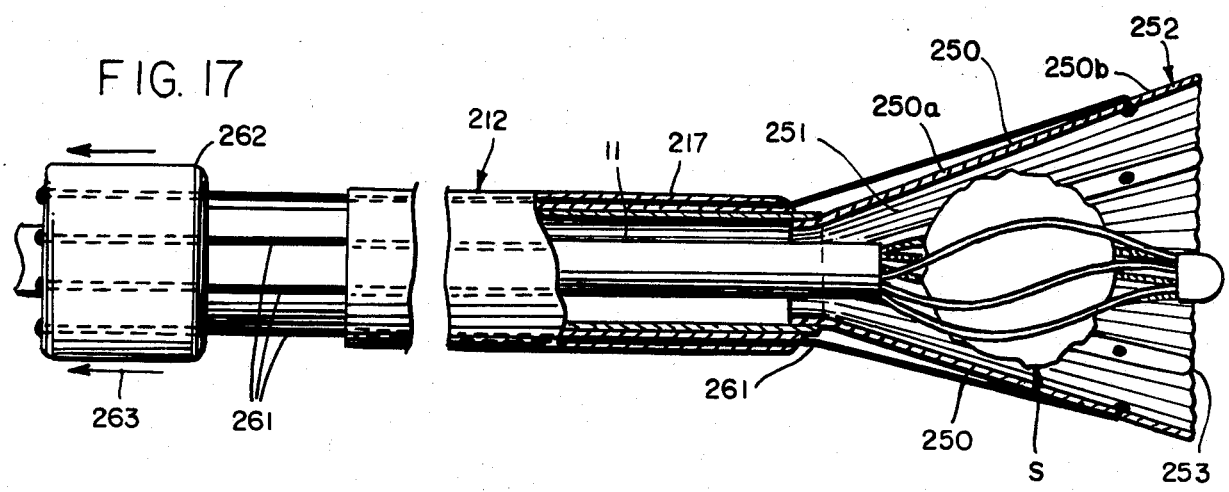

FIG. 17 is a fragmentary longitudinal sectional view similar to FIG. 16 but showing the basket in its fully expanded condition as a captured stone is being retracted therein.

Figure 18:
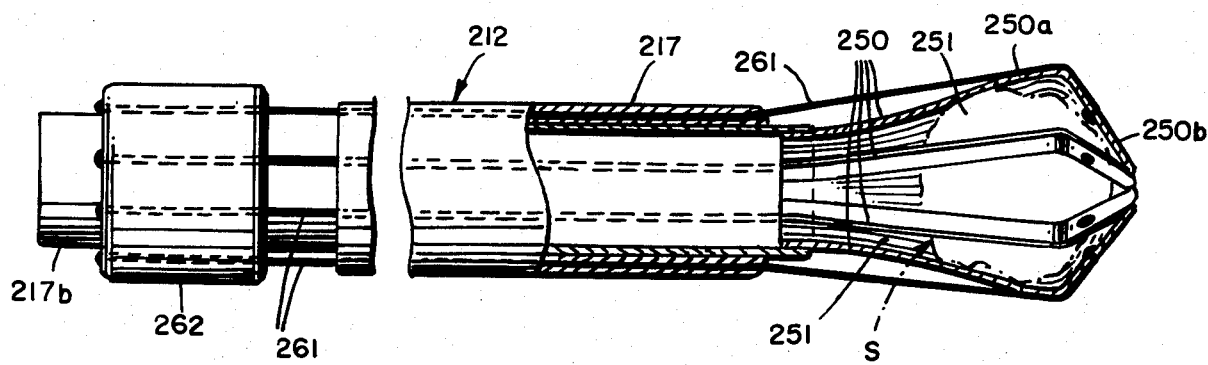

FIG. 18 is a sectional view similar to FIG. 17 but showing the catheter as it would appear with a stone retained within the basket-providing distal end portion thereof (the grasping device being omitted for clarity of illustration).

FIG. 19 is an enlarged fragmentary longitudinal sectional view of the distal end of an instrument constituting a fourth embodiment of the invention.

FIG. 20 illustrates the instrument of FIG. 19 with the basket in its fully expanded condition.

FIG. 21 shows the fourth embodiment as it would appear with a stone captured and retained within the basket.

DETAILED DESCRIPTION OF PREFERRED EMBODIMENTS

Figure 1:
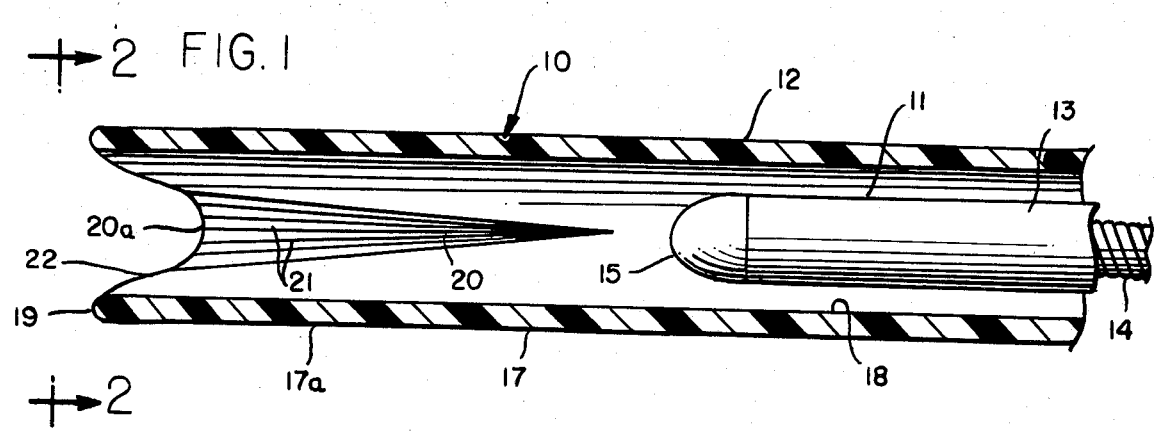
FIG. 1 is a fragmentary longitudinal sectional view of the distal end of an instrument embodying the invention, such instrument including a catheter and a grasping device.

Referring to the drawings, and particularly to FIGS. 1 and 8, the numeral 10 generally designates an instrument comprising an inner stone grasping device 11 and an outer catheter 12. The grasping device may be a conventional "stone basket" of the type disclosed, for example, in Pat. Nos. 4,046,150 and 2,943,626, such device including a smooth outer tube 13 containing a stranded wire cable 14 that terminates in a protective tip 15 at the working end of the device. When the cable is extended distally, as shown in FIGS. 4–7, spring wire strands 14a at the working end expand to form a cage 16 which may be used to entrap a stone or calculus 17. Since such structure is well known in the art and fully disclosed in the above-identified patents, further description is believed unnecessary herein. It is to be emphasized, however, that device 11 is only one type of stone grasping device that might be used as an element in the combination of this invention and that other types of grasping devices, particularly the miniaturized flexible grasping forceps also in common use, may be used in place of the wire cage structure.

Figure 2:
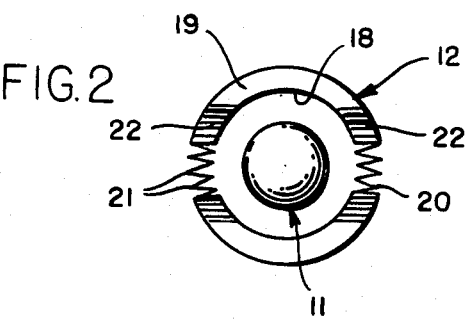
FIG. 2 is an elevational view taken along line 2—2 of FIG. 1.
Figure 3:
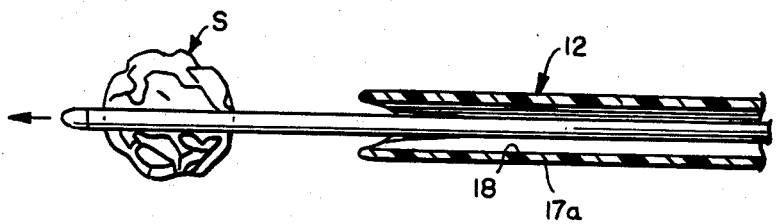
Figure 4:
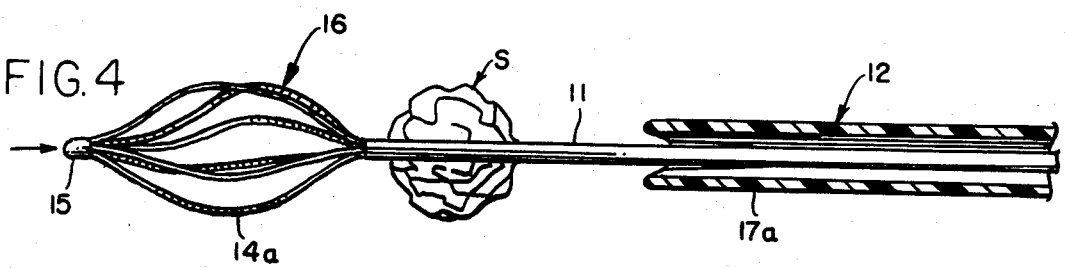
Figure 5:
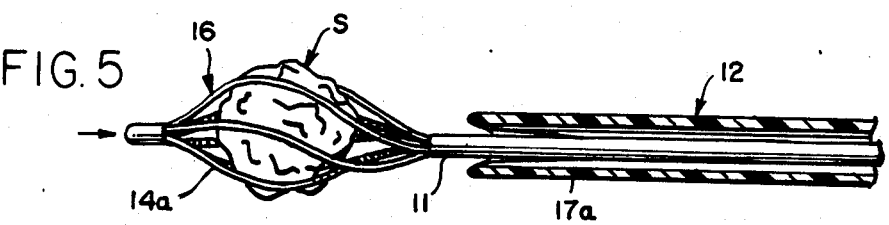

Catheter 12 has an elongated body 17 terminating in proximal and distal end portions. As shown most clearly in FIGS. 1 and 2, the body defines a lumen 18 of generally uniform circular cross section. The catheter is formed of a tough flexible material such as polyethylene or polypropylene, but other polymeric and non-polymeric materials (e.g., thin metals having sufficient flexibility and durability) might also be used.

Expansion and contraction of the catheter's distal end portion 17a is facilitated by at least one gusset, and preferably a plurality of gussets, provided in the wall of the distal portion. Two such gussets 20, diametrically disposed, are depicted. Gussets 20 may be formed as an integral part of the catheter and, to provide sufficient expandability, are relatively thin and may be provided with a plurality of longitudinal folds 21. Alternatively, the gussets may be formed as separate components secured by heat sealing or by any other suitable means within an excised or cut-out portion of the catheter, in which case each gusset may be formed of an elastomeric material capable of being joined securely to the remainder of the catheter. It will be noted from FIGS. 1 and 8 that the expandable gussets 20 are generally triangular in configuration and their distal ends 20a are spaced rearwardly or proximally behind the edge of the catheter defining distal openings 19. Specifically, the leading end 20a of each gusset 20 forms the rear or proximal margin of a recess 22 formed in the end portion of the catheter.

Figure 6:
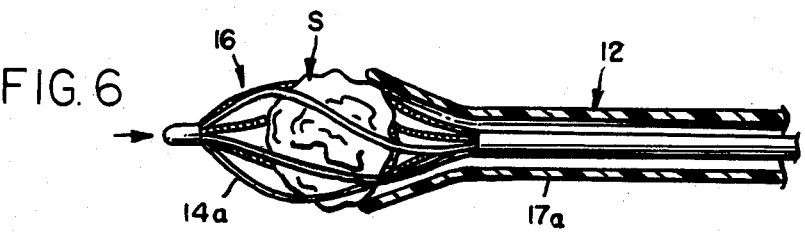

In use of the instrument, the grasping device 11 and catheter 12 are advanced translumenally or percutaneously to the site of the calculus. The working end of the grasping device is then extended from the distal end portion of the catheter to grasp the stone and draw it into the basket or receiving chamber at the catheter's distal end. If the grasping device is of the type shown in the drawings, then the cage 16 is expanded after the tip of the device has been advanced beyond stone S (FIG. 4); then, as the device 11 is retracted the stone is captured within the cage (FIG. 5) and drawn into the distal end of the catheter (FIGS. 6, 7). Gussets 20 expand to receive the captured stone and the working end of the grasping device. Once the stone is located well within the distal portion of the catheter (preferably at about the longitudinal midpoint of gussets 20), the stone becomes substantially enclosed with the extreme distal portion of the catheter adjacent opening 19 returning to essentially its original cross sectional dimensions (FIGS. 7, 9).

With the stone so contained, the entire instrument (catheter 12 and grasping device 11) may be retracted without danger that the edges of the stone might cut or otherwise injure delicate tissues. The catheter therefore provides a protective enclosure to prevent or reduce the possibility of injury as the stone is extracted. If desired, stone S may be fragmented in situ, while it is confined within the distal portion of the catheter, by any suitable fragmenting means. Where the grasping device takes the form of a stone basket (as shown), the fragmenting means may be an ultrasonic generator extended through the coiled wire 14 as disclosed in Pat. No. 4,046,150. Other types of lithotriptors may be used, including an electrohydraulic lithotriptor. Regardless of the manner of fragmentation, the distal portion of the catheter 12 that confines the stone tends to protect the surrounding tissue during fragmentation process and also tends to retain the fragments during removal of the instrument.

It is believed apparent that the dimensions of the catheter and its components may be varied depending on the size of the calculus to be captured and confined, the location of the calculus (whether in the kidney, ureter, bladder, or bile tract), the type of grasping device utilized, the in situ treatment (if any) of the stone, and other medical considerations. However, to insure adequate confinement of the stone, it has been found that the expandable distal portion of the catheter, which may be regarded as approximating the length of gussets 20, should be about 0.5 inches or more. A length within the range of 0.5 to 1.5 inches is believed particularly effective.

In the embodiment depicted in FIGS. 10–15, the grasping device 11 is shown for purposes of illustration to be identical to the grasping device already described, it being understood that any of the alternative grasping devices discussed above may also be utilized. Catheter 112 has an elongated body 117 terminating at one end in a distal portion 117a equipped with a plurality of circumferentially-spaced struts 150 bridged by a thin film or webbing of tough, flexible, pliant, and preferably stretchable (and recoverable) material. The webs or webbing 151 may be formed of an elastomer such as silicone rubber, but any of a variety of other materials (such as plasticized vinyl or polyurethane) may be suitable. The webbing is joined to the struts, either internally or externally (as shown), by heat sealing, adhesive bonding, or any other suitable means. The struts in turn have their proximal ends embedded, fused, adhered, or otherwise secured to the remainder of the catheter body 117. While stainless steel is believed particularly effective as a fabricating material for the struts, other materials might be used.

Struts 150 and webbing 151 define a basket or stone receiver 152 which assumes the open condition depicted in FIGS. 13 and 14 when the struts 150 are substantially untensioned. Under such conditions, each of the struts is somewhat L-shaped in configuration, having a proximal portion 150a and a distal portion 150b. Portions 150a radiate outwardly and distally, whereas portions 150b project less outwardly and more distally, terminating in an enlarged entrance opening 153 for the basket or stone receiver.

Means are provided for closing the basket, such means taking the form of a flexible outer tube 154 that slidably receives catheter body 117, the elongated outer tube having a distal end 155 engagable with the struts when the catheter is drawn in a proximal direction. When fully collapsed, the basket or stone receiver appears as shown in FIG. 11 with the opening 153 substantially fully closed. Opening of the basket is achieved by urging the catheter body 117 in a distal direction in relation to outer tube 154, such manipulations being directed from the proximal ends of the catheter and flexible outer tube. FIG. 11 depicts the instrument in the condition it would assume as its distal end is advanced to the site of the calculus. The outer tube 154 is then retracted (or the catheter advanced) as illustrated in FIGS. 12-13, until the stone receiver 152 assumes an opened condition. The grasping device is advanced through the lumen of the catheter to capture the stone and draw it into the chamber of the basket or stone receiver (FIGS. 14 and 15). The basket is then at least partially closed by retracting the catheter body 117 with respect to outer tube 154, thereby confining the stone within the chamber of the stone receiver (FIG. 15). The stone may be extracted intact or may first be fragmented in situ, all as previously described.

FIGS. 16-18 present a third embodiment of the instrument in which a flexible catheter 212 again has an elongated tubular body 217 equipped at its distal end with a plurality of circumferentially-spaced flexible struts 250. The struts may be formed from stainless steel or any other suitable material and secured to the catheter body as already indicated. However, unlike struts 150 of the second embodiment, struts 250 normally assume the distally-projecting and converging positions depicted in FIG. 16 when such struts are in untensioned (or substantially untensioned) condition and the basket 252 is closed. Also, each of the struts 250 has a forwardly-extending proximal portion 250a and a normally forwardly- and inwardly-turned distal portion 250b, the two portions being hinged together for flexion and extension. Ideally, the hinge 260 is formed integrally with portions 250a and 250b and may take the form of a transverse score line which restrains the distal portion 250b from pivoting outwardly at the hinge line beyond a position of general longitudinal alignment with portion 250a (FIG. 17). Webbing 251, as described in connection with the embodiment of FIGS. 10-15, joins all of the struts together, the webbing being normally folded or collapsed, but being expandable and stretchable when the struts are flexed into the tensioned condition, with the stone receiver or basket 252 fully opened, as illustrated in FIG. 17.

Catheter body 217 may be formed integrally or as two permanently-joined concentric tubes 217a and 217b. In either case, the catheter wall is provided with longitudinal channels or passages through which flexible actuating lines 261 extend. Each line or filament extends through the outer tubular portion 217a of the catheter body and is connected at its proximal end to a suitable actuating mechanism such as, for example, an operating sleeve 262 slidably carried by inner tubular portion 217b or by a handle extension of that portion. At their distal ends, the filaments extend about the hinges of the struts and then continue inwardly where they are permanently connected to the struts' distal portions 250b.

FIG. 16 shows the catheter with its distal end in collapsed condition but with the grasping device omitted for clarity of illustration, it being understood that at the time of use, and certainly at the time a calculus has been located and the tip of the catheter has been advanced to the site of the calculus, the grasping device 11 would be contained within the catheter and readied for use. The basket or stone receiver at the distal end of the catheter is then opened by shifting collar 262 in a proximal direction as indicated by arrow 263 (FIG. 17). The grasping device 11 is advanced to capture stone S, and the stone is retracted through opening 253 and into the basket or receiver 252. Thereafter, the operating collar is shifted in a distal direction, allowing the tensioned struts to return as far as possible into their original closed positions. The stone is thereby contained within the receiving chamber of the catheter as depicted in FIG. 18 (the grasping device 11 again being omitted, and stone S being shown in phantom, for clarity of illustration). The captured and confined stone may then be withdrawn intact or, as previously described, may be fragmented in situ prior to removal.

Like the third embodiment, the fourth embodiment of FIGS. 19-21 has a catheter 312 with an elongated tubular body 317 terminating at its distal end in a plurality of circumferentially spaced struts 350 defining a basket or stone receiver 352 that is normally in closed condition (FIG. 19). Each strut has a proximal portion 350a that extends forwardly and outwardly, and a distal portion 350b that extends forwardly and inwardly when the struts are untensioned but, when the basket is fully expanded, such distal portions extend forwardly and outwardly as depicted in FIG. 20.

Webbing 351 takes the form of a thin, flexible, outer covering or sleeve that encloses the struts and is secured to them only adjacent their distal ends. In contrast to the webbing of prior embodiments, the flexible webbing 351 should be of only limited stretchability since it functions not only as the enclosing membrane of the basket but also as the connecting means for urging that basket into opened condition. Specifically, the webbing extends proximally about struts 350 and is joined at its proximal end to a flexible outer tube 354 that slidably receives catheter body 317. To expand the basket 352, the outer tube is urged in a proximal direction in relation to catheter 312, thereby tensioning webbing 351 and pulling the struts outwardly into the open positions shown in FIG. 20. The grasping device 11 is then advanced through the lumen of the catheter to capture the stone S and draw it into the chamber of the basket or stone receiver. By shifting the outer tube distally with respect to the catheter, the tension struts are allowed to close about the captured stone (FIG. 21). The stone may then be extracted intact or may be fragmented in situ as previously described.

An inherent feature of this invention, especially apparent in the embodiments of FIGS. 11-21, is that catheter expansion serves to enlarge the soft tissue passages in a way that might permit movement and extraction of a stone even if the grasping device were not used or remained inoperative. In short, the catheter may function to dialate a body passage and, should such dialation then result in movement of the calculus in the direction of the catheter, removal of the stone might be possible either by allowing it to travel into the expanded distal end of the catheter and then retracting the catheter, or by progressively retracting the expanded end of the catheter immediately in advance of the moving calculus.

While in the foregoing embodiments of the invention have been disclosed in considerable detail for purposes of illustration, it will be understood by those skilled in the art that many of these details may be varied without departing from the spirit and scope of the invention.

We claim:

1. An instrument for calculus containment and removal, comprising an elongated stone grasping device having a distal working end for grasping calculi; a catheter having a lumen slidably receiving said grasping device; said catheter having a body formed of flexible material and having distal and proximal end portions; said distal end portion terminating in an opening through which said work end of said grasping device may be extended and retracted for the purpose of grasping a stone and drawing it into said catheter; said distal end portion of said catheter being expandable to receive a stone retained by said working end of said grasping device and contractable to at least partially envelope said stone and working end; said distal end portion of said catheter including a plurality of elongated circumferentially-spaced flexible struts, each having proximal and distal sections, defining a basket for receiving a stone retained by said grasping device; said distal sections of said struts converging towards each other, with said basket in substantially closed condition, when said struts are in first positions of adjustment and diverging distally outwardly to enlarge said basket and provide a distal entrance therefor when said struts are in second positions of adjustment; web means of flexible and foldable material bridging adjacent struts for substantially the full length thereof; and strut adjusting means located outside the lumen of said catheter and outside of said struts for externally engaging said struts and shifting the same between their first and second positions of adjustment.

2. The instrument of claim 1 in which said struts are in said second positions of adjustment when in normal, substantially unintensioned condition; said strut adjusting means comprising a flexible actuating tube slidably mounted upon said catheter; said tube having a distal end engagable with said struts for urging the same into said first positions of adjustment to close said basket when said tube is shifted distally in relation to said catheter.

3. The instrument of claim 2 in which said actuating tube is engagable with the proximal sections of said struts for moving said struts into said first positions of adjustment; said distal sections having their free ends adjacent to each other when said struts are in said first positions of adjustment.

4. The instrument of claim 2 in which said basket has maximum outside cross sectional dimensions less than those of said actuating tube when said struts are in their first positions of adjustment.

5. The instrument of claim 1 in which said struts are in said first positions of adjustment when in normal substantially untensioned condition; said strut adjusting means including a plurality of control lines extending longitudinally through said catheter and connected distally to said struts and proximally to a control member movable along the axis of said catheter at the proximal end portion thereof.

6. The instrument of claim 1 in which said struts are in said first positions of adjustment when in normal, substantially untensioned condition; said strut adjusting means comprising sleeve means of thin, flexible material extending about said struts and connected to the distal ends thereof; and operating means associated with said catheter for urging said sleeve means proximally to pull said struts outwardly into tensioned second positions of adjustment wherein said struts are spread apart to enlarge said basket and provide a distal opening therefor, and for relieving the pulling force on said sleeve means to allow said struts to return into their normal first positions of adjustment.

7. The instrument of claim 6 in which said operating means comprises a flexible actuating tube slidably mounted upon said catheter; said tube having a distal end engagable with the proximal end of said sleeve means for shifting said sleeve means axially to open and close said basket.

8. A catheter for use with a stone grasping device having a distal working end for grasping calculi, said catheter having a lumen for slidably receiving a stone grasping device and having a body formed of flexible material and provided with distal and proximal end portions; said distal end portion terminating in an opening through which the working end of a grasping device may be extended and retracted for the purpose of grasping a stone and drawing it into said catheter; said distal end portion of said catheter being expandable to receive a stone retained by the working end of a grasping device and contractable to at least partially envelope the stone and the working end of a grasping device; said distal end portion of said catheter including a plurality of elongated circumferentially-spaced flexible struts, each having proximal and distal sections, defining a basket for receiving a stone retained by a grasping device; said distal sections of said struts converging towards each other, with said basket in substantially closed condition, when said struts are in first positions of adjustment and diverging distally outwardly to enlarge said basket and provide a distal entrance therefor when said struts are in second positions of adjustment; said struts being in said first positions of adjustment when in normal, substantially untensioned condition; sleeve means of thin, flexible material extending about said struts for substantially the full length thereof and connected to the distal ends thereof; and operating means associated with said catheter for urging said sleeve means proximally to pull said struts outwardly into tensioned second positions of adjustment wherein said struts are spread apart to enlarge said basket and provide a distal opening therefor, and for relieving the pulling force on said sleeve means to allow said struts to return into their normal first positions of adjustment; said operating means comprising a flexible actuating tube slidably mounted upon said catheter; said actuating tube having a distal end connected to the proximal end of said sleeve means for shifting said sleeve means axially to open and close said basket.

* * * * *